United States Patent [19]

Bara et al.

[11] Patent Number: 5,478,555
[45] Date of Patent: Dec. 26, 1995

[54] COSMETIC COMPOSITION FOR THE MAKE-UP OF THE SKIN, CONTAINING AT LEAST ONE SILICONE WAX AND PROCESS FOR ITS PREPARATION

[75] Inventors: Isabelle Bara, Paris; Myriam Mellul, L'Hay Les Roses, both of France

[73] Assignee: L'Oreal, Paris, France

[21] Appl. No.: 230,833

[22] Filed: Apr. 21, 1994

Related U.S. Application Data

[63] Continuation of Ser. No. 935,877, Aug. 26, 1992, abandoned.

[30] Foreign Application Priority Data

Aug. 30, 1991 [FR] France ................ 91 10792

[51] Int. Cl.$^6$ .................. A61K 7/021; A61K 7/031; A61K 7/035
[52] U.S. Cl. .................... 424/78.03; 424/78.02; 424/63
[58] Field of Search .................. 424/78.02, 78.03, 424/63

[56] References Cited

U.S. PATENT DOCUMENTS

| | | | |
|---|---|---|---|
| 4,855,129 | 8/1989 | Steinbach et al. | 424/63 |
| 5,073,372 | 12/1991 | Turner et al. | 424/401 |
| 5,223,559 | 6/1993 | Arraudeau et al. | 424/78.31 |
| 5,236,710 | 8/1993 | Guerrero et al. | 424/78.02 |
| 5,326,557 | 7/1994 | Glover et al. | 424/78.03 |
| 5,380,528 | 1/1995 | Alban et al. | 424/401 |

FOREIGN PATENT DOCUMENTS

| | | |
|---|---|---|
| 0106762 | 4/1984 | European Pat. Off. . |
| 2528699 | 12/1983 | France . |
| 2123290 | 2/1984 | United Kingdom . |

OTHER PUBLICATIONS

French Search Report for FR 91 10792.

*Primary Examiner*—Peter F. Kulkosky
*Attorney, Agent, or Firm*—Cushman Darby & Cushman

[57] ABSTRACT

Composition in which the silicone wax(es) is (are) dispersed in an aqueous phase containing two water-soluble acrylic polymers; the first type of polymer(s) consists of at least one copolymer of a $C_3$–$C_6$ monoethylenic acid or of its anhydride, and the second type of polymer(s) consists of at least one acrylic acid polymer or one of its salts. The presence of these two water-soluble acrylic polymers allows the dispersion of silicone wax(es) to be stabilised.

5 Claims, No Drawings

COSMETIC COMPOSITION FOR THE MAKE-UP OF THE SKIN, CONTAINING AT LEAST ONE SILICONE WAX AND PROCESS FOR ITS PREPARATION

This is a continuation of application Ser. No. 07/935,877, filed Aug. 26, 1992, now abandoned.

The present invention relates to a cosmetic composition for the make-up of the skin, containing at least one silicone wax in the form of dispersion in an aqueous phase, this composition being stable without it being necessary to introduce a surface-active agent therein.

Products for making up the skin are frequently emulsions of a fatty phase in an aqueous phase; it is obviously necessary that such an emulsion should be stable in the course of time to acceptable commercially. The stability of the said emulsions is generally ensured by incorporating surface-active agents into them. Unfortunately, the presence of surface-active agents is frequently a source of discomfort or skin irritation and it is desirable to avoid it.

In skin make-up compositions such as lipsticks and eye shadows it is often advantageous to employ a wax and not an oil as constituent of the fatty phase, so as to obtain more consistent products which can be applied in the form of a cake or stick. It is desired, in particular, to employ silicone waxes because the said waxes have advantageous cosmetic properties: good spreadability, high film-forming capacity, gloss and water resistance. Until now, however, it has been practically impossible to prepare, using waxes, surfactant-free emulsions which are stable in the course of time and which contain a high percentage of wax(es). Be that as it may, with silicone waxes even the presence of surfactants does not solve the problem: as soon as the percentage of silicone wax was raised, a coalescence of the silicone wax generally took place and course and relatively unstable emulsions were obtained, which could not be employed for making up the skin.

A make-up composition consisting of an oil-in-water dispersion whose stability is ensured by virtue of the incorporation of crosslinked acrylic polymers in the aqueous phase has already been proposed in Patent Application JP-02-019,310. Similarly, EP-A- 268,164 has described the stabilization of an oil-in-water emulsion with the aid of acrylic polymers. Nevertheless, in the fatty phase of these two make-up compositions only oils are found and never silicone waxes; and it has turned out, in fact, that silicone waxes are not stabilized by the systems described.

The objective of the present invention is to obtain a stable dispersion of at least one silicone wax in an aqueous phase, the said dispersion having a high silicone wax content without it being necessary to add surface-active agents. According to the invention this objective is obtained by combining two particular acrylic polymers with the silicone wax(es) in the aqueous phase.

The subject of the present invention is therefore a cosmetic composition for the make-up of the skin, containing at least one silicone wax, characterized in that the silicone wax(es) is (are) dispersed in an aqueous phase containing two types of water-soluble acrylic polymer(s), the first type of polymer(s) consisting of at least one copolymer of a $C_3$–$C_6$ monoethylenic acid or of its anhydride with a long-chain acrylic ester, and the second type of these polymer(s) consisting of at least one homo- or copolymer of acrylic acid or one of its salts, copolymers of acrylic acid with a long chain acrylic ester and their salts being excluded from said second type of polymers.

It has been found, according to the invention, that the presence of these two types of acrylic polymers is necessary to obtain, in an aqueous phase, a stable dispersion of silicone wax(es), containing more than 10% by weight of silicone wax and that it makes it possible to obtain stable dispersions containing up to 60% by weight of silicone wax(es).

The first type of water-soluble acrylic polymer(s), which will be called "modified polymer" in the text which follows, is described in EP-A-0,268,164. This modified polymer is an optionally crosslinked copolymer of a monoethylenic carboxylic acid containing 3 to 6 carbon atoms (or of its anhydride) and of a long-chain acrylic ester. The proportion of monomeric acid in this copolymer is preferably from 90 to 98% by weight and the proportion of monomeric ester is preferably from 10 to 2% by weight.

The monomeric acid has the formula:

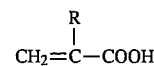

in which formula R denotes H, a halogen, OH, a lactone or lactam radical, a —C≡N group or an alkyl, aryl, aralkyl, alkylaryl or cycloaliphatic radical. The preferred acidic monomers are acrylic acid and maleic anhydride.

The monomeric ester has the formula:

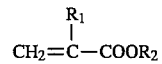

in which formula:

$R_1$ is H, methyl or ethyl and $R_2$ is a $C_8$–$C_{30}$ alkyl, $C_8$–$C_{30}$ oxyalkylene or $C_8$–$C_{30}$ carbonyloxyalkylene radical. $C_{10}$–$C_{22}$ alkyl radicals are preferred. Among the monomeric esters which are preferred there may be mentioned decyl, lauryl, stearyl, behenyl and melissyl acrylates and methacrylates.

The modified polymers employed according to the invention are distributed in the trade at least in the case of some of them; they are, for example, marketed under the name "PEMULEN®" by B. F. Goodrich.

The second type of water-soluble acrylic polymer(s) is an optionally crosslinked acrylic acid homo- or copolymer or one of its salts; the copolymers of acrylic acid with a long chain acrylic ester and their salts, which are included in the first type of water-soluble acrylic acid are excluded. The second type water-soluble polymers are selected, for example, from those marketed under the name "CARBOPOL®" by B.F. Goodrich under the name "HOSTACERIN®" (copolymer of sodium acrylate and acrylamide) or under the name "PAS 5161" (copolymer of ammonium acrylate and acrylamide) by Hoeschst.

The first type of polymer(s) or "modified polymer" is present in proportions of between 0.001 and 1% by weight relative to the total weight of the composition, and preferably between 0.02 and 0.2% by weight.

The second type of polymer(s) is present in proportions of between 0.2 and 2% by weight relative to the total weight of the composition, and preferably between 0.4 and 1.5% by weight.

The silicone waxes employed are those generally employed in cosmetics. Among these, more particular mention may be made of the organosilanes which have the following formula:

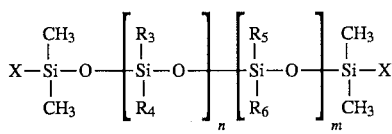

in which formula:

$R_3$, $R_5$ and $R_6$ are, independently of each other, a $C_1$–$C_{30}$ alkyl or alkoxy radical or a $C_6$–$C_{30}$ aryl radical;

$R_4$ is a $C_2$–$C_{36}$ alkyl or alkoxy radical or a $C_2$–$C_{36}$ alkyl or alkoxy radical substituted by an ester group, it being also possible for $R_4$ to be a methyl radical when X is a $C_2$–$C_{30}$ alkyl or alkoxy radical or a $C_2$–$C_{30}$ ester;

X is a $C_1$–$C_{30}$ alkyl or alkoxy radical, a $C_6$–$C_{30}$ aryl radical or a $C_1$–$C_{30}$ ester;

n is an integer between 1 and 100, m is 0 or an integer between 1 and 100.

It is possible, for example, to mention the alkyldimethicone marketed under the name "ABIL WAX 9810®" by Goldschmidt, the dibehenoxydimethicone marketed under the name "ABIL WAX 2440®" by Goldschmidt or the stearoxydimethicone marketed under the name "VP 1622®" by Wacker.

It is also possible to employ the organosiloxanes obtained by the action of a natural wax, such as carnauba wax or beeswax on a reactive silicone backbone.

The silicone wax represents from 10 to 60% by weight relative to the total weight of the composition. In the case of quantities of waxes which are smaller than 10% it is possible to obtain emulsions of silicone wax(es) in the absence of the two types of polymer(s) of the present invention; in the case of quantities greater than 60% by weight it is no longer possible to obtain emulsions which are stable in the course of time.

The aqueous phase of the silicone wax emulsion may contain water-soluble polymers other than the two types of acrylic polymer(s) necessary for making use of the invention. These other water-soluble polymers may be:

protein derivatives and, more particularly, keratin derivatives such as keratin hydrolysates and sulphonic keratins;

cellulose derivatives such as hydroxyethyl cellulose, hydroxypropyl cellulose, methyl cellulose, ethyl hydroxyethyl cellulose and carboxymethyl cellulose;

natural polymers such as gums arabic and xanthan derivatives;

polyvinylpyrrolidones, and polyvinyl alcohol.

The aqueous phase may also contain alcohols or polyols which are generally employed in cosmetics, such as ethanol, glycerine, polyglycerines or any other water-soluble ingredient.

The silicone wax(es) may be mixed with waxes which are traditionally generally employed in cosmetics, such as animal waxes (beeswaxes, lanolin), vegetable waxes (carnauba wax, candelilla wax), mineral waxes (paraffins, ozokerites, microcrystalline waxes) or synthetic waxes (polyethylene waxes). In such a mixture the silicone wax(es) represents (represent) preferably at least 20% by weight relative to the total weight of the waxes of the composition and at least 10% by weight relative to the total weight of the composition.

The cosmetic composition may also contain colored fillers and/or colorless fillers.

The colored fillers are inorganic, organic and/or pearlescent pigments.

By way of examples of inorganic pigments there may be mentioned titanium dioxide (rutile or anatase) optionally surface-treated, and codified in the Colour Index (C.I.) under reference CI 77891, black, yellow, red and brown iron oxides codified under references CI 77499, 77492 and 77491, manganese violet (CI 77742), ultramarine blue (CI 77007), chromium oxide (CI 77288), chromium hydrate (CI 77289) and ferric blue (CI 77510).

Organic pigments are chosen particularly from carbon black, the pigments D & C Red No. 19 (CI 45170), D & C Red No. 9 (CI 15585), D & C Red No. 21 (CI 45380), D & C Orange No. 4 (CI 15510), D & C Orange No. 5 (CI 45370) D & C Red No. 27 (CI 15850), D & C Red No. 6 (CI 15850), D & C Yellow No. 5 (CI 45425), D & C Yellow No. 6 (CI 15985), D & C Red No. 30 (CI 73360), D & C Red No. 3 (CI 45430) and cochineal carmine-based lakes (CI 75470).

The pearlescent pigments may be chosen especially from the group consisting of mica coated with titanium oxide, bismuth oxychloride, titanium mica with iron oxides and titanium mica with ferric blue or chromium oxide.

When employed, the pigments generally represent from 0.5 to 20% by weight of the total weight of the composition.

The colorless pigments are chosen especially from the group consisting of:

talc, which is a magnesium silicate hydrate employed in the form of particles which are generally smaller than 40 μm in size;

micas, which are aluminosilicates of various compositions, which are in the form of flakes from 2 to 200 μm in size, preferably from 5 to 70 μm and with a thickness of 0.1 to 5 μm, preferably from 0.2 to 3 μm, it being possible for these micas to be of natural origin (for example muscovite, margarite, roscoelite, lipidolite, biotite) or of synthetic origin;

starch, in particular rice starch;

kaolin, which is an aluminum silicate hydrate and is in the form of particles of isotropic shape generally smaller than 30 μm in size;

zinc and titanium oxides, generally employed in the form of particles whose size does not exceed a few micrometers (or even smaller than 1 μm in the case of titanium oxide);

calcium carbonate;

magnesium carbonate or hydrocarbonate;

microcrystalline cellulose;

powdered synthetic polymers such as polyethylene, polyesters (for example polyethylene isophthalate or terephthalate), polyamides, Teflons and hollow or solid crosslinked powdered silicones.

When employed, the fillers may represent up to 40% by weight relative to the total weight of the composition.

The pigments and the fillers may be coated in a known manner with substances such as amino acids, silicones, metal salts or collagen, or may have been subjected to a treatment allowing the surface state to be modified.

The compositions according to the invention may also contain at least one inert or active compound which is generally employed in cosmetic compositions, taken especially from the groups consisting of emollients, preserving agents, sequestrants, perfumes, oils, including silicone oils, alkalifying or acidifying agents for adjusting the pH of the composition, and vitamins, amino acids or other active substances.

A further subject of the present invention is a process for the manufacture of the composition according to the invention, in which, in a first stage, the silicone wax(es), optionally mixed with other waxes, is (are) mixed at a temperature above the melting point and the liposoluble additive(s) is (are) optionally incorporated; in a second stage the fatty phase obtained is mixed with the solid filler(s); in a third stage an aqueous phase is prepared containing the two types of water-soluble acrylic polymer(s) and optionally other water-soluble polymers as well as water-soluble active substances; and, in a fourth stage, the fatty phase obtained in the second stage is added to the said aqueous phase and the fatty phase is dispersed in the aqueous phase by mechanical agitation.

The examples given below, purely by way of illustration and without any limitation being implied, will allow the invention to be better understood.

EXAMPLE 1: MAKE-UP FOUNDATION

A composition which has the following formulation by weight is prepared:

| | |
|---|---|
| Alkylated carboxyvinyl polymer sold under the trade name "PEMULEN TR2 ®" by Goodrich | 0.1% |
| Carboxyvinyl acid polymer sold under the name "CARBOPOL 940 ®" by Goodrich | 0.6% |
| Triethanolamine | 0.8% |
| Water q.s. | 100% |
| Polydimethylsiloxanol in a cyclomethicone sold under the trade name "Q2-1401 ®" by Dow Corning | 5% |
| Alkyldimethicone sold under the trade name "ABIL WAX 9810 ®" by Goldschmidt | 4% |
| Alkoxydimethicone sold under the trade name "ABIL WAX 2440 ®" by Goldschmidt | 11% |
| Cyclomethicone sold by Dow Corning | 5% |
| Glycerine | 3% |
| Preserving agent q.s. | |
| Titanium dioxide | 4% |
| Yellow iron oxide | 1.43% |
| Red iron oxide | 0.55% |
| Black iron oxide | 0.22% |

A waxy make-up foundation is obtained, which is stable in the course of time, can be applied with a sponge, is original in texture, very soft and matt.

EXAMPLE 2: EYE SHADOW

A composition which has the following formulation by weight is prepared:

| | |
|---|---|
| Alkylated carboxyvinyl polymer sold under the trade name "PEMULEN TR2 ®" by Goodrich | 0.1% |
| Ammonium acrylate and acrylamide copolymer sold under the trade name "PAS 5161 ®" by Hoechst | 1.5% |
| Polydimethylsiloxane sold under the trade name "Q2-1403 ®" by Dow Corning | 5% |
| Triethanolamine | 0.1% |
| Dibehenoxydimethicone sold under the trade name "ABIL WAX 2440 ®" by Goldschmidt | 5% |
| Stearoxydimethicone sold under the trade name "VP 1622 ®" by Wacker | 10% |
| Glycerine | 5% |
| Pigments | 12.5% |
| Preserving agent q.s. | |
| Water q.s. | 100% |

The shadow obtained is creamy, stable in the course of time, can be spread with a finger or with the applicator, is soft and easy to spread and behaves well.

EXAMPLE 3: BLUSHER

A composition which has the following formulation by weight is prepared:

| | |
|---|---|
| Alkylated carboxyvinyl polymer sold under the trade name "PEMULEN TR2 ®" by Goodrich | 0.1% |
| Sodium acrylate and acrylamide copolymer sold under the trade name "HOSTACERIN ®" by Hoechst | 1.2% |
| Triethanolamine | 0.1% |
| Stearoxydimethicone sold under the trade name "VP 1621 ®" by Wacker | 15% |
| Cyclomethicone | 10% |
| Polydimethylsiloxane sold under the name "Q2-1403 ®" by Dow Corning | 5% |
| Glycerine | 5% |
| Preserving agent q.s. | |
| Pigments | 7.9% |
| Water q.s. | 100% |

A very soft blusher is obtained, which is stable in the course of time, easy to spread with a finger or sponge and which behaves well.

We claim:

1. A cosmetic make-up composition for the skin consisting essentially of a stable dispersion of (a) a silicone wax in an aqueous phase in the absence of a surface-active agent, said silicone wax being present in an amount ranging from 10 to 60 percent by weight based on the total weight of said composition, (b) said aqueous phase also containing a first water-soluble acrylic polymer, present in an amount ranging from 0.001 to 1 percent by weight based on the total weight of said composition, said first water-soluble acrylic polymer consisting of a copolymer of (i) a $C_3$–$C_6$ monoethylenic acid or anhydride present in an amount ranging from 90 to 98 weight percent with (ii) a long chain acrylic ester present in an amount ranging from 10 to 2 weight percent, and (c) said aqueous phase also containing a second water-soluble acrylic polymer consisting of a homo- or copolymer of acrylic acid or a salt thereof, said second water-soluble acrylic polymer being present in an amount ranging from 0.2 to 2.0 percent by weight based on the total weight of said composition, said second water-soluble acrylic polymer excluding a copolymer of acrylic acid with a long chain acrylic ester or a salt thereof, said first water-soluble acrylic polymer having the formula

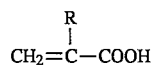

wherein R represents H, halogen, OH, a lactone radical, a lactam radical, —C≡N, alkyl, aryl, aralkyl, alkylaryl or cycloaliphatic and said first water-soluble long chain acrylic ester having the formula

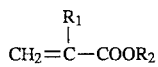

wherein $R_1$ represents H, methyl or ethyl and $R_2$ represents $C_8$–$C_{30}$ alkyl, $C_8$–$C_{30}$ oxyalkylene or $C_8$–$C_{30}$ carbonyloxyalkylene.

2. The cosmetic make-up composition of claim 1 wherein said first water-soluble acrylic polymer is present in an amount ranging from 0.02 to 0.2 percent by weight based on the total weight of said composition.

3. The cosmetic make-up composition of claim 1 wherein said second water-soluble acrylic polymer is a copolymer of an acrylic acid salt and acrylamide.

4. The cosmetic make-up composition of claim 1 wherein said second water-soluble acrylic polymer is present in an amount ranging from 0.4 to 1.5 percent by weight based on the total weight of said composition.

5. The cosmetic make-up composition of claim 1 wherein said silicone wax is an organosiloxane having the formula

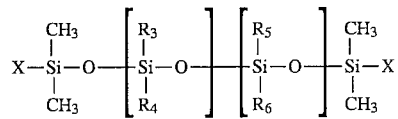

wherein $R_3$, $R_5$ and $R_6$, each independently, represent $C_1$–$C_{30}$ alkyl, $C_1$–$C_{30}$ alkoxy or $C_6$–$C_{30}$ aryl, $R_4$ represents $C_2$–$C_{36}$ alkyl, $C_2$–$C_{36}$ alkoxy, $C_2$–$C_{36}$ alkyl substituted by an ester, $C_2$–$C_{36}$ alkoxy substituted by an ester, methyl when X is (i) $C_2$–$C_{30}$ alkyl, (ii) $C_2$–$C_{30}$ alkoxy or (iii) $C_2$–$C_{30}$ ester, X represents $C_1$–$C_{30}$ alkyl, $C_1$–$C_{30}$ alkoxy, $C_6$–$C_{30}$ aryl or $C_1$–$C_{30}$ ester, n is an integer ranging from 1 to 100; and m is 0 or an integer ranging from 1 to 100.

* * * * *